US010271823B2

(12) United States Patent
Keshet (10) Patent No.: US 10,271,823 B2
(45) Date of Patent: Apr. 30, 2019

(54) EXTRACTING A CARDIAC-CYCLE SIGNAL FROM ECHOCARDIOGRAM DATA (71) Applicant: General Electric Company, Schenectady, NY (US)

(72) Inventor: Renato Keshet, Haifa (IL)

(73) Assignee: General Electric Company, Schenectady, NY (US)

( * ) Notice: Subject to any disclaimer, the term of this patent is extended or adjusted under 35 U.S.C. 154(b) by 75 days.

(21) Appl. No.: 15/722,788

(22) Filed: Oct. 2, 2017

(65) Prior Publication Data
US 2019/0099162 A1 Apr. 4, 2019

(51) Int. Cl.
A61B 8/00 (2006.01)
A61B 8/02 (2006.01)
A61B 8/08 (2006.01)
G06T 3/40 (2006.01)
G06T 7/00 (2017.01)

(52) U.S. Cl.
CPC .............. A61B 8/5223 (2013.01); A61B 8/02 (2013.01); A61B 8/0883 (2013.01); A61B 8/463 (2013.01); G06T 3/40 (2013.01); G06T 7/0016 (2013.01); G06T 2207/10016 (2013.01); G06T 2207/10132 (2013.01); G06T 2207/30048 (2013.01)

(58) Field of Classification Search
CPC ....... A61B 8/5223; A61B 8/02; A61B 8/0883; A61B 8/463; G06T 3/40; G06T 7/0016; G06T 2207/10016; G06T 2207/10132; G06T 2207/30048
See application file for complete search history.

(56) References Cited

U.S. PATENT DOCUMENTS

| 6,277,075 | B1 | 8/2001 | Torp et al. |
| 7,477,771 | B2 | 1/2009 | Iatrou et al. |
| 7,678,050 | B2 | 3/2010 | Aase et al. |
| 7,751,875 | B2 | 7/2010 | Bojovic et al. |
| 8,323,198 | B2 | 12/2012 | Tirumalai et al. |
| 8,790,264 | B2 | 7/2014 | Sandler et al. |
| 9,161,724 | B2 | 10/2015 | Hautvast et al. |
| 2017/0119255 | A1 | 5/2017 | Mahajan et al. |

FOREIGN PATENT DOCUMENTS

WO 2011075429 A1 6/2011

OTHER PUBLICATIONS

Park, Jinah, et al.; "Deformable Models with Parameter Functions for Cardiac Motion Analysis from Tagged MRI Data", IEEE Transactions on Medical Imaging, http://ieeexplore.ieee.org/document/500137/, pp. 278-289, vol. 15, Issue 03, Jun. 1996.

(Continued)

Primary Examiner — Brenda C Bernardi
(74) Attorney, Agent, or Firm — Ernest G. Cusick (57) ABSTRACT The present approach relates to extracting a heart cycle signal from ultrasound sequences (e.g., echocardiograms) without complex spatial image processing and without finding or assuming the knowledge of the position of heart reference points. The present heart cycle signal is computed by determining temporal changes in low-resolution versions of the echocardiographic frames, such as temporal information of the heartbeat.

20 Claims, 6 Drawing Sheets (56) References Cited

OTHER PUBLICATIONS

Yang, Hui, et al.; "Spatiotemporal Representation of Cardiac Vectorcardiogram (VCG) Signals", BioMedical Engineering OnLine, https://biomedical-engineering-online.biomedcentral.com/articles/10.1186/1475-925X-11-16, Mar. 30, 2012.

Yang, Hui, et al.; "Identification of myocardial infarction (MI) using spatio-temporal heart dynamics", Medical Engineering & Physics, http://www.sciencedirect.com/science/article/pii/S1350453311002190, pp. 485-497, vol. 34, Issue 04, May 2012.

EXTRACTING A CARDIAC-CYCLE SIGNAL FROM ECHOCARDIOGRAM DATA

BACKGROUND

The subject matter disclosed herein relates to extracting heart motion and cycle information from ultrasound based data, such as an echocardiogram.

Physicians may use a variety of non-invasive techniques to obtain patient cardiac information. Such cardiac information may include time signals that may be used to understand the function of a patient's heart, such as signals that may be used to characterize cardiac cycles. By way of example, signals such as a phonocardiogram (which records heart sounds, similarly to what may be heard through a stethoscope) and an electrocardiogram (i.e., an ECG, which records electrical activity through electrodes positioned on the patient) may provide timing information relevant to cardiac events of interest. Pressure and volume signals may also be obtained, but often require invasive approaches to acquire. These signals have a range of applications, from heart-rate (HR) estimation through diagnosis of pathologies.

Another modality that is increasingly pervasive in cardiac analysis is the echocardiogram, which employs an ultrasound scanner to view the heart. Echocardiogram frames make it relatively easy for healthcare providers to observe, in a noninvasive manner, the heart's anatomy and mechanical function, and qualitatively inspect its contractility, valve dynamics, volume, and so forth.

Despite the many benefits of the echocardiogram, its two-dimensional (2D)-spatial nature makes the assessment of time-related information, such as heart rate and/or the duration of different cardiac phases, less direct. When searching for the exact frame that corresponds to the end of systole, for instance, a physician might scroll through an echocardiogram frame sequence until visually identifying the image or frame when the displayed ventricles are at their minimum volume, which may be time consuming and imprecise. For this reason, it is common to augment the display of echocardiograms with a concurrently displayed electrocardiogram (ECG). This helps physicians to readily obtain the heart rate and to navigate to key frames of the echocardiogram corresponding to a given cardiac phase or electrical event based on the concurrently displayed ECG.

However, there are various situations in which it is typically not possible or convenient to attach ECG electrodes to a patient. For example, this may be true in primary care contexts and in emergency medical contexts, where patient evaluation and/or treatment may be time-sensitive, and thus poorly suited to the laborious electrode placement process typical of ECG acquisition. In these situations, the benefits provided by the concurrent display of the ECG are lost.

BRIEF DESCRIPTION

In one embodiment, a method for generating a cardiac-cycle signal is provided. In accordance with this method, an echocardiogram comprising a first sequence of image frames is accessed or acquired. Each image frame of the first sequence is resized to generate a second sequence resized image frames. A first matrix is generated in which one of its dimensions corresponds to a sequence of flattened versions of the resized image frames. At least a second matrix is derived from the first matrix. The second matrix is a unitary matrix whose columns or rows are left-singular vectors of the first matrix. The cardiac-cycle signal is generated using one singular vector of the second matrix. The cardiac-cycle signal is displayed on a monitor.

In a further embodiment, an ultrasound imaging system is provided. In accordance with this embodiment, the ultrasound imaging system includes processing circuitry configured to: acquire an echocardiogram comprising a first sequence of image frames; resize each image frame of the first sequence to generate a second sequence resized image frames; generate a first matrix in which one of its dimensions corresponds to a sequence of flattened versions of the resized image frames; derive from the first matrix at least a second matrix, wherein the second matrix is a unitary matrix whose columns or rows are equal to or approximations of singular vectors of the first matrix; generate the cardiac-cycle signal using one singular vector of the second matrix; and display the cardiac-cycle signal on a monitor.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The present approach relates to obtaining a cardiac-cycle signal (from which time-related information can be determined) that is extracted from an echocardiogram. In certain implementations discussed herein the cardiac-cycle signal is obtained in an automated manner and in real-time. One benefit of such a signal is the ability to use it in place of an ECG when it is impractical to acquire ECG data, such as in emergency or other time-sensitive contexts. Other potential applications include, but are not limited to, the diagnosis of certain pathologies, either alone or in conjunction with an ECG.

With respect to prior approaches in this area, a number of surrogate ECG solutions have previously been proposed, however, such surrogate ECG solutions suffer from various failings. For example, one approach that has been proposed extracts intensity curves from the echocardiogram and analyzes the sum of absolute differences for the cycle length (i.e., heart rate, HR) estimation. In order to determine the cycle start, a deformable model is fitted to the left ventricle in real-time, and used by a speckle-tracking procedure. In another approach, several heart features, such as the mitral valve, are automatically detected and their movement analyzed by an artificial neural network. In such approaches a time signal is not explicitly produced, but the approaches instead compute the heart rate and cycle phases without explicit timing data to associate with the associated echocardiogram. In another proposed approach, a time signal is produced by measuring the mean intensity on a chosen window on the left ventricle, which is also detected in real-time.

As may be appreciated, the above solutions rely heavily on spatial processing of some (or all) of the sequence images, in order to determine the position of reference points in the images, such as the left ventricle center or walls, the basal point, the mitral or tricuspid valves, or others. Such image processing is computationally intensive, and therefore relatively slow, and is not robust, as it incurs in the risk of finding the wrong position for those reference points.

Another research area that produces a time signal that characterizes the cardiac cycle is that of strain analysis. Strain-rate curves are cardiac parameters than can be obtained from tissue Doppler imaging (TDI) or speckle-tracking echocardiography (STE). These approaches characterize the myocardial function by measuring the amount of tissue strain and relaxation during systole and diastole, respectively.

However, these approaches are also computationally intensive. STE requires discovery of ventricle walls and accurately tracking their movements, and therefore assumes good to high image quality of the echocardiogram, as well as employing complex algorithms for determining the ventricle walls and computing their movements. In particular, speckles seen in the tissue imaging are automatically tracked from frame to frame, and this data is averaged in space and time to improve robustness. TDI, on the other hand, uses echocardiography Doppler effects to determine movement, which is faster and more robust, but requires accurate detection of the tissue to be examined, and focusing of the ultrasound wave on that tissue for Doppler imaging capture. Tissue detection also requires good-to-high image quality for the algorithm to work robustly.

Thus, known approaches for obtaining a non-ECG cardiac-cycle signal from an echocardiogram typically heavy spatial processing on each of the sequence images of the echocardiogram to determine the position of reference points in the images, such as the left ventricle center or walls, the basal point, the mitral or tricuspid vales, or others. As noted, such image processing is very computationally intensive and is not robust as it incurs in the risk of finding the wrong position for the reference points.

In contrast, the present approach generates a cardiac-cycle signal (which is also denoted herein as a heart cycle signal or a mechanical cardiogram (MCG)) that can be used to determine the heart phases using cardio-ultrasound sequences without the image processing required by conventional approaches and in a fast, simple, and robust manner. In particular, the present approach, in contrast to prior approaches, relies mainly on the temporal information of the heart sequences (e.g., the temporal changes on the intensities of the pixels throughout the ultrasound image sequence), rather than the spatial information (i.e., identification and tracking of structures in the images), to derive the cardiac-cycle signal for an acquired echocardiogram. In this manner, the present approach requires no complex image processing and no detection of specific objects or structures within the images. The extracted cardiac-cycle signal is highly correlated with ventricular volume over time as well as with strain rate. As such, the cardiac-cycle signal can be used for several applications, including heart rate (HR) estimation, cardiac cycle phase determination, navigation to key echocardiogram frames (such as end-of-systole and end-of-diastole), and detection of arrhythmia, without the assistance of an electrocardiogram (ECG). Thus, the present approach can be implemented on ultrasound devices or accompanying software (e.g., software written in Python) suitable for ultrasound products, to provide cardiac information such as the heart rate, beginning and end of systole and diastole, as well as other heart phase events.

Figure 1:
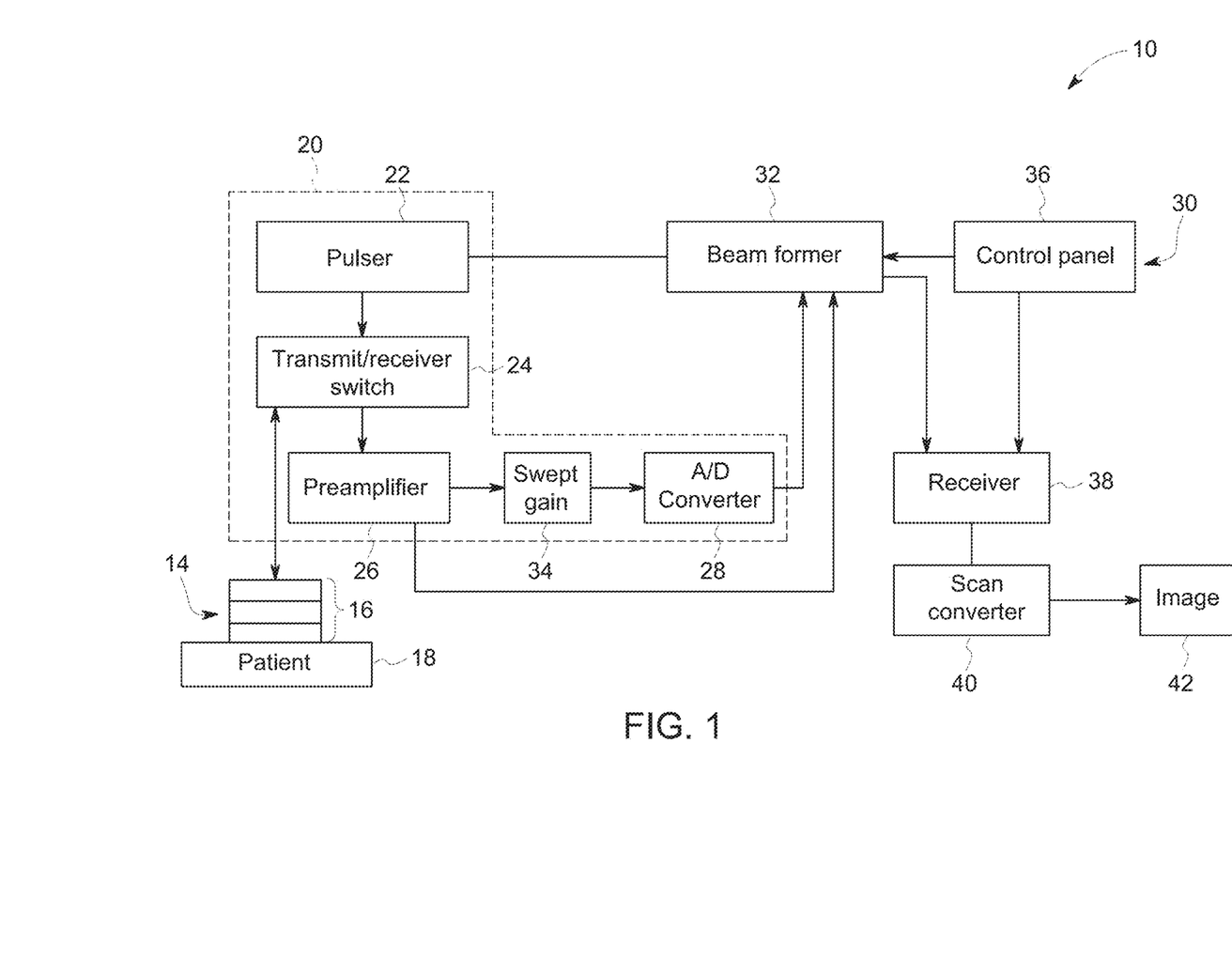
FIG. 1 is an embodiment of a block diagram of an ultrasound system, in accordance with aspects of the present disclosure.

With the preceding in mind, and by way of providing useful context, FIG. 1 depicts a high-level view of components of an ultrasound system 10 that may be suitable in the implementation of the present approach. In particular, the present approach may be implemented as one or more executable routines stored on memory or data storage components of the system 10 (such as of the control panel 36) and/or by one or more application specific integrated circuits (ASICs) of the system 10. The illustrated ultrasound system 10 includes a transducer array 14 having transducer elements 16 suitable for contact with a subject or patient 18 during a cardiac imaging procedure. It should be noted that the transducer array 14 is configured as a two-way transducer and capable of transmitting ultrasound waves into and receiving such energy from the subject or patient 18. In transmission mode, the transducer array elements 16 convert the electrical energy into ultrasound waves and transmit it into the patient 18. In reception mode, the transducer array elements 16 convert the ultrasound energy received from the patient 18 (backscattered waves) into electrical signals.

Each transducer element 16 is associated with respective transducer circuitry 20. That is, in the illustrated embodiment, each transducer element 16 in the array 14 has a pulser 22, a transmit/receive switch 24, a preamplifier 26, a swept gain 34, and an analog to digital (A/D) converter 28. In other implementations, this arrangement may be simplified or otherwise changed. For example, components shown in the circuitry 20 may be provided upstream or downstream of the depicted arrangement; however, the basic functionality depicted will typically still be provided for each transducer element 16.

Further, a variety of other imaging components 30 are provided to enable image formation with the ultrasound system 10. Specifically, the depicted example of an ultrasound system 10 also includes a beam former 32, a control panel 36, a receiver 38, and a scan converter 40 that cooperate with the transducer circuitry 20 to produce an image or series of images 42 (e.g., an echocardiogram) that may be stored and/or displayed to an operator, such as in conjunction with an extracted heart cycle signal as discussed herein. A processing component (e.g., a microprocessor) and a memory of the system 10, such as may be present control panel 36, may be used to execute stored routines for processing the acquired ultrasound cardiac images to generate a cardiac-cycle signal and/or motion frames, as discussed herein, which may be displayed on a monitor of the ultrasound system 10.

With the preceding system level discussion in mind as useful context, the present approach computes a cardiac-cycle signal (referred to in certain instances herein as a mechanical cardiogram (MCG) or heart cycle signal) from echocardiogram frames (e.g., images 42) without complex image processing and in a very fast, simple, and straightforward way. It may be noted that as used herein the frames of the electrocardiogram may also be referred to as image frame or images, such as image 42, as each frame in the sequence is also a distinct image. Likewise, though a step or explanation herein may be presented in the context of an image, it should be appreciated that such images may in sequence constitute the frames of an echocardiogram or other video presentation.

As previously noted, this process is done by relying primarily on the temporal information of the heart sequences (e.g., pixel intensity changes), rather than high-resolution spatial information. In particular, as discussed in greater detail below, the present approach is directed to representing the changes in a cardiac image sequence as well as possible by a single vector (which constitutes the cardiac-cycle signal) such that the cardiac-cycle signal is the vector that best captures the heart dynamics for the given sequence. Because its values are on the time axis, this cardiac-cycle signal vector can be viewed as a time signal. As shown herein, the cardiac-cycle signal, or MCG, is highly correlated with ventricular volume, an example of which is shown with a corresponding ECG in FIG. 2 for reference. The cardiac-cycle signal also resembles strain-rate curves, as they are also typically correlated with the ventricular volume.

Figure 3:
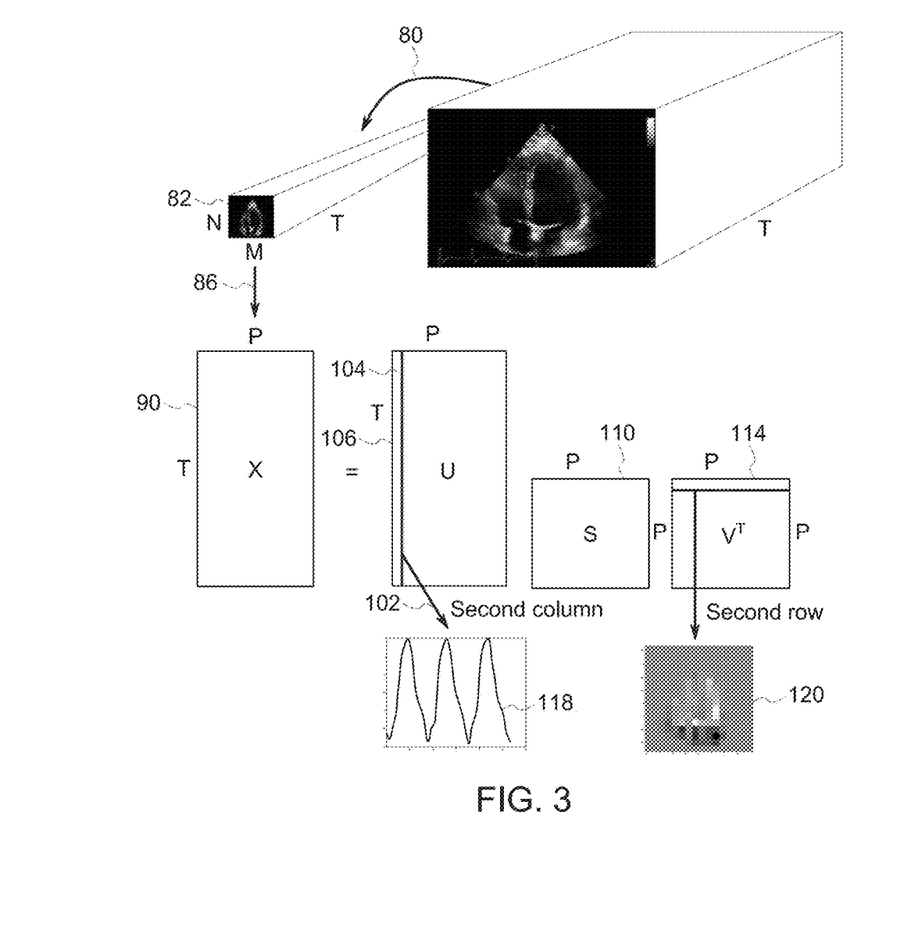
FIG. 3 is a process flow illustrating steps of an algorithm for computing a cardiac-cycle signal and a motion frame, in accordance with aspects of the present disclosure.

With the preceding in mind, computation of the cardiac-cycle signal is illustrated as a diagrammatic process flow in FIG. 3. With respect to the present discussion and the following examples, certain references may be made to matrices and to the rows and columns of such matrices. For the sake of explanation, and to simplify discussion, certain operations may be characterized as being in relation to a given column of a respective matrix. However, it will be appreciated by those or skill in the art that such characterizations, both in the discussion and following claims, may be equivalently characterized in terms of a row instead (such as a row of a transpose of the respective matrix) without a change in meaning or scope. That is, in view of the present teachings, it should be understood that the concept of row and column within a matrix may be viewed as mathematically equivalent depending on the transposition state of a given matrix. Hence, both within the present discussion and the attached claims it should be understood that the terms row and column should be understood to be interchangeable and equivalent within the context of a matrix and its transposition.

As discussed in greater detail below, the basic computation algorithm performs the steps of resizing (i.e., spatially downscaling) the images of an ultrasound sequence to generate corresponding low resolution (i.e., N×M) frames or images 82 (e.g., 16×16 images). A T×(N×M) matrix, X, is generated where each row contains the pixels of one of the resized ultrasound image 82 (i.e., each row of X is one flattened frame 82). To simplify presentation of certain materials herein, the term (N×M) is simplified to P in certain instances, so it should be understood below that the terms P and (N×M) are mathematically interchangeable for the present purpose. The matrix X is decomposed into matrices $U \cdot S \cdot V^t$. The second column of the matrix U constitutes the cardiac cycle signal of interest, which describes how the heart moves over time throughout the echocardiogram being evaluated.

With respect to the mathematical basis of the decomposition process a singular value decomposition (SVD) of X is contemplated. Mathematically, the singular value decomposition of the T×P matrix X (reference number 90) is a factorization of the form $X = U \cdot S \cdot V^t$, where U (reference number 106) is a T×P unitary matrix, S (reference number 110) is a P×P rectangular diagonal matrix with non-negative real numbers on the diagonal, and V (reference number 114) is an P×P unitary matrix. The diagonal entries $\sigma_i$ of S are known as the singular values of X. The columns of U and the columns of V are called the left-singular vectors and right-singular vectors of X, respectively.

This singular value decomposition may be viewed as a generalization of the eigendecomposition of a positive semi-definite normal matrix (such as, a symmetric matrix with positive eigenvalues) to any N×M matrix. In such a context, the following observations may be made: (1) the left-singular vectors of X are a set of orthonormal eigenvectors of $XX^t$ and a vector v is an eigenvector of $XX^t$ when there exists a scalar λ for which $XX^t v = \lambda v$. The scalar λ may then be referred to as an eigenvalue of $XX^t$; and (2) the right-singular vectors of X are a set of orthonormal eigenvectors of $X^tX$. The non-zero singular values of X (found on the diagonal entries of S) are the square roots of the non-zero eigenvalues of both $XX^t$ and $X^tX$.

One interpretation of the SVD that may be useful in the present context is its value as a low-rank matrix approximation. For example, suppose one needs to solve the problem of approximating a matrix X with a different, truncated matrix $\tilde{X}$ having a specific rank r. In an application in which the approximation is based on minimizing the difference between X and $\tilde{X}$ under the constraint that rank $(\tilde{X}) = r$, the solution is given by the SVD of $X = U \cdot S \cdot V^t$, namely $\tilde{X} = U \cdot \tilde{S} \cdot V^t$, where $\tilde{S}$ is the same matrix as S except that it contains only the r largest singular values, with the other singular values being replaced by zeroes.

In this case, S also satisfies:

$$\tilde{S} = U_r \cdot S_r \cdot V_r^t \qquad (1)$$

where $U_r$ is a T×r matrix consisting of the first r columns of U, $S_r$ is the r×r diagonal matrix consisting of the first r singular values, and $V_r$ is the P×r matrix consisting of the first r columns of V.

Thus, with the preceding mathematical basis in mind, and turning back to the diagrammatic process flow of FIG. 3, it may be seen that the present approach is directed to representing the changes in a cardiac image sequence, such as may be associated with an echocardiogram, as a single vector to the extent possible. This vector (i.e., the cardiac-cycle signal or MCG as used herein) is the vector that best captures the heart dynamics for the given sequence of images 42, and because its entries are on the time axis, one can see this vector also as a time signal.

Thus, turning back to FIG. 3 with the mathematical background provided above, it may be appreciated that the present approach attempts to approximate the whole sequence of frames or images 42 of an echocardiogram by a low-rank matrix (e.g., r=1, r=2, and so forth) with singular value decomposition procedures being employed to provide a solution. The present approach represents the sequence of images by a matrix X, where the first dimension relates to the time axis and the second dimension relates to the spatial axis (the pixels), and compute its SVD. By keeping only the left-singular vectors with largest singular values, the approximation is achieved.

More formally, let $\{I_0, I_1, \ldots, I_{T-1}\}$ be a sequence of T cardiac images 42, where T>1. A low-resolution sequence $\{I_0', I_1', \ldots, I_{T-1}'\}$ of T images 82 is computed (step 80) where each image frame $I_n'$ is a spatially downscaled version of $I_n$ having resolution N×M (e.g., 16×16 pixel images). The matrix X (reference number 90) is generated (step 86) with T rows and (N×M) columns, where row t contains the pixels of the frame $I_t'$ in a flattened manner. It does not matter the manner the flattening is done, as long as it is the same for all frames. The singular value decomposition of the matrix X is computed, i.e., the unitary matrices U (reference number 106) and V (reference number 114) are computed, as well as the diagonal matrix S (reference number 110), such that $X = U \cdot S \cdot V^t$. The second column 104 of U is retrieved (step 102) and is the cardiac-cycle signal 118 for the given sequence of images 42 that describes how the heart moves overt time throughout the input sequence (i.e., sequence of images 42). In particular, the first singular-vectors (left and right) relate mostly to the average frame (i.e., "DC component" in signal processing terms), thus the singular-vectors that best capture the movement in the sequence are the second ones, here second column 104.

The above approach for computing a cardiac-cycle signal 18 (i.e., a heart cycle signal) from echocardiogram data, was tested using M=N for values of 2, 4, 8, 16, 32, 64, and 128. The cardiac-cycle signal output 118 was robust within this range and the obtained signals were consistent in their temporal features.

In addition, as discussed herein, the second column of V may also be extracted and provides an indication of which pixels are most active, that is, which pixels change the most throughout the sequence, which is indicative of motion. This second column of V is denoted herein as the motion frame 120 of the sequence of images 42 and may be presented or displayed as a low-resolution N×M image. In particular, the reason the second vectors (columns) are retrieved (rather than, for instance, the first) is that, while the first column of V returns approximately the "average frame" of the sequence (i.e., the average motion), the second column of V returns the pixels that most deviate from that "average frame", which corresponds to the pixels that change (or move) the most. Thus, the second column of V describes how those "most-active" pixels have changed in time throughout the sequence of images 42.

Figure 4:
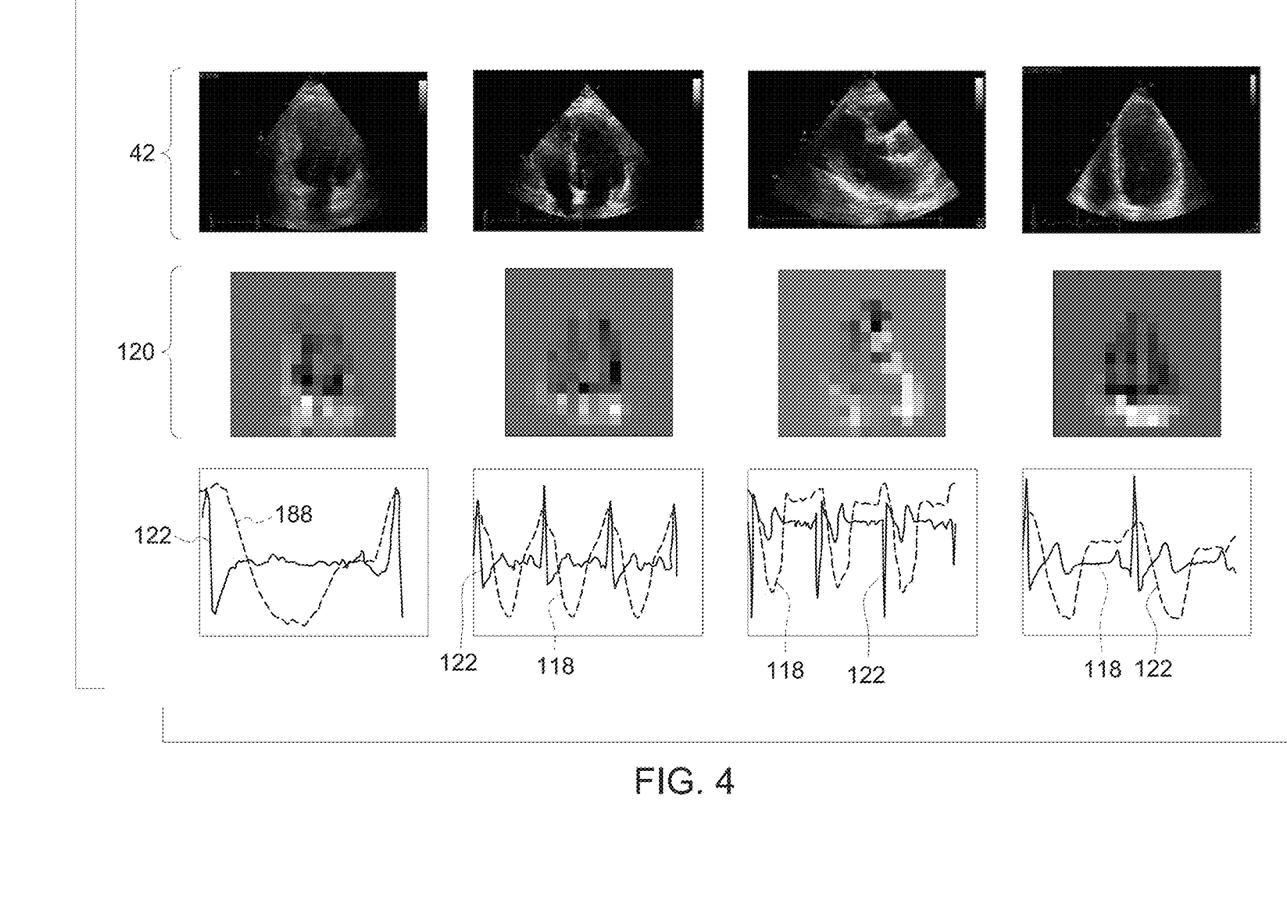
FIG. 4 depicts examples of echocardiogram frames and extracted motion frames and cardiac-cycle signals, in accordance with aspects of the present disclosure.

To visually illustrate both the cardiac-cycle signal and motion frame aspects of the present approach, FIG. 4 shows four examples, with each column of figures corresponding to a different echocardiogram. The first row of images depicts the first frame of the echocardiogram of the respective example (i.e., the first frame in a stack of images 42 forming the respective cardiogram). Images 42 in these stacks may be at full pixel resolution (e.g., 1000×700, 600×800, 400×600, and so forth). The second row of images depicts the computed motion frames 120 for each echocardiogram in the respective example. In the depiction of the motion frames, pixel intensity corresponds to motion, with higher intensity pixels (i.e., darker pixels) exhibiting negative or less motion than lower intensity (i.e., white or lighter pixels), which correspond to positive or greater motion. The motion frame images 120 may correspond in scale to the lower-resolution images down-sampled from the original images 42, and thus may be at a lower resolution, such as 16×16 pixels. The third row graphically illustrates a cardiac-cycle signal 118 computed for each respective echocardiogram as discussed herein superimposed on a concurrently obtained ECG 122.

Figure 5:
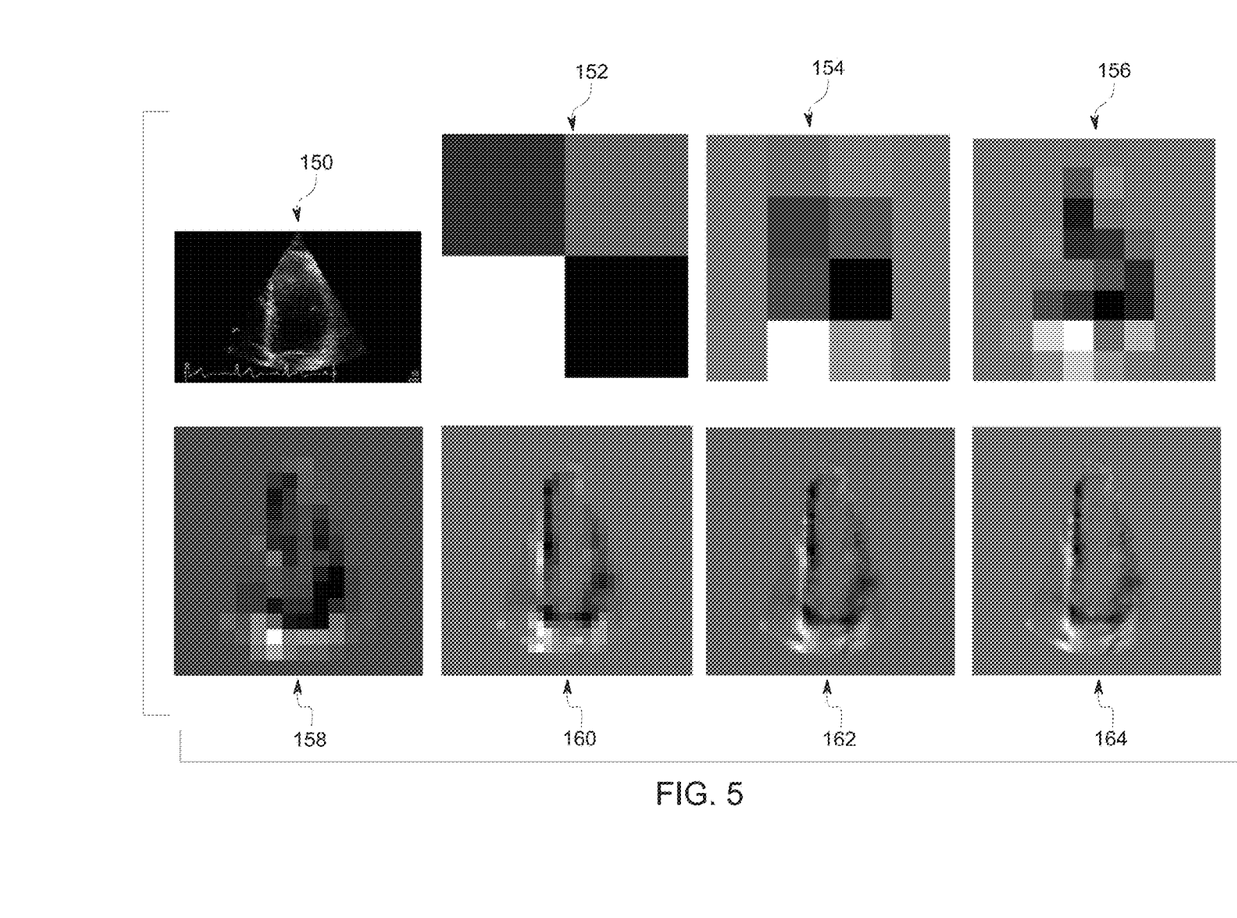
FIG. 5 depicts motion frames at different resolutions, in accordance with aspects of the present disclosure.

FIG. 5 depicts examples of computed motion frames 120 at different resolutions. As noted above, pixel intensity corresponds to motion, with the brightest and darkest pixels indicating the positions of pixels that changed the most and opposite color pixels (i.e., black and white) indicating opposite motion directions (e.g., when the dark areas are contracting, the bright ones are relaxing, and vice-versa). In the depicted example, reference number 150 refers to a frame of the original echocardiogram sequence, and reference numbers 152, 154, 156, 158, 160, 162, and 164 referring to motion frames 120 where N=M=2, 4, 8, 16, 32, 64, and 128 pixels, respectively.

Turning back to the algorithmic aspects of the approach, it may be seen from equation (1), that $X \cdot V_r \cdot S_r^{-1} = U_r$, and therefore each left-singular-vector $u_n$ in $U_r$ is equal to the projection of the sequence X onto the corresponding right-singular-vector $v_n$, normalized by the corresponding singular value $\sigma_n$, that is:

$$u_n = X \cdot \frac{v_n}{\sigma_n} \qquad (2)$$

From equation (2) one can see that the cardiac-cycle signal (i.e., $u_2$) is in fact a weighted average of the columns of X, where the weights are given by the values in the motion frame ($v_2$) divided by $\sigma_2$. Each column of X is a time signal, describing the motion of a particular low-res pixel. The values of $v_2$ represent the pixels that changed ("moved") the most throughout the sequence. The cardiac-cycle signal (i.e., MCG) is then the average time signal, weighted according to the motion intensity. This aspect enables a method for online computation of the cardiac-cycle signal, as discussed below.

While the preceding illustrates aspects one implementation of computing a cardiac-cycle signal, it may be appreciated that such a signal may be computed in other manners as well. For example, in an alternative implementation of this algorithm an improved cardiac-cycle signal and motion frame may be obtained, but with a trade-off of increased computational intensity. In particular, the contemplated alternative implementation is similar to the algorithm described above, but computes the average row $\bar{x}$ of matrix X, subtracts $\bar{x}$ from each row of X before the SVD operation is performed, and retrieves the first column of U as cardiac-cycle signal and first column of V as motion frame, instead of the respective second columns.

This alternative adds the steps of computing $\bar{x}$, as well as subtracting this term from every row in X. However, this approach provides a more accurate set of "most-active" pixels in the motion frame 120, and thus a more accurate cardiac-cycle signal. Such improvements, however, are incremental and may not be justified in view of the additional computational requirement.

With respect to the present approach, it may also be noted that the cardiac-cycle signal 118 extracted by either the basic or alternative algorithms suffers from a polarity ambiguity inherent to the singular value decomposition (SVD) procedure. This following discussion relates further algorithmic steps that may be employed to solve this ambiguity for typical cases.

With this in mind, the ambiguity at issue arises in view of the observation that, if a vector v is a right-singular-vector for a given matrix A (and thus v is an eigenvector of $A^t$ A), then the vector −v is also a right-singular-vector of A. Indeed, when $A^t$ A·v=λv for some scalar λ, then $A^t$ A·(−v)=λ(−v) is also true.

Therefore, the SVD procedure in the basic or alternative algorithm can yield v as a motion frame or −v. If the motion frame v corresponds a cardiac-cycle signal u, then the corresponding cardiac-cycle signal for −v is −u. In other words, the SVD procedure can produce the desired signal as well as its mirror image, and one cannot know a priori which one the algorithm will yield.

As discussed herein, this ambiguity can generally be solved in view of the following observations. First, because the ventricles move in the opposite direction of the atria (in most clinical contexts), motion-frame pixels associated with these different structures will have opposite signs; e.g., if ventricle pixels in the motion frame are positive, then those of the atria will be negative, and vice-versa. This effect can be observed in FIG. 4, where dark and light pixels are generally observed on opposite vertical sides of the imaged region.

Second, during systole, the ventricles contract, whereas the atria expand. As a consequence, pixels in the ventricle will become brighter (less blood, which is seen as dark on ultrasound), while the atria will become darker. Then, when the ventricle pixels in the motion frame are positive, the cardiac-cycle signal will increase during systole. In the present context, it is desired for the cardiac-cycle signal (i.e., the MCG) to correlate well with ventricular volume (as discussed below), so the cardiac-cycle signal should decrease during systole. Thus, a goal is to have the ventricular pixels in the motion frame be negative.

With these points in mind, one algorithmic approach for solving the ambiguity can be formulated, though one requirement is imposed: that the center of mass of the ventricles appear above that of the atria in the echocardiogram sequence frames (i.e., images 42). This requirement is met for most of the standard echocardiogram views (e.g., parasternal long, all apical views, sub-costal). When that is the case, one can inspect the motion frame image 120 and check if the upper part is predominantly darker than the lower part. If not, then both the cardiac-cycle signal 118 and the motion frame 120 are inverted. When it cannot be determined that the ventricles are above the atria, the polarity of the cardiac-cycle signal 118 cannot be reliably determined, though the signal can still be used for heart rate extraction, which is indifferent to signal polarity.

With this in mind, one example of an algorithm for addressing polarity disambiguity includes the steps of: (a) Let s(r) be the sum of the motion frame's row r; (b) Let c(r) be the convolution of the function s(r) with the step kernel k(r), where $$k(r) = \begin{cases} 1 & r \leq 0 \\ -1 & r > 0 \end{cases} \quad (3)$$

that is:

$$c(r) = \sum_{r'=1}^{N} s(r')k(r - r') \quad (4)$$

(c) let ρ be the maximum of |c(r)|; (d) multiply the MCG (and the motion frame) by −1 if:

$$\sum_{r < \rho} s(r') > 0 \quad (5)$$

Turning back to the cardiac-cycle signal (i.e., MCG), the following observations may be made with respect to the properties and physical model of this signal. First, the cardiac-cycle signal 118, as discussed herein typically has a high correlation with the ECG signal 122, as can generally be seen in FIG. 4. In particular, it can be seen that the MCG cyclic period is equal to that of the ECG. One can therefore obtain the heart rate (HR) from the cardiac-cycle signal 118, just like one can from the ECG 122.

Figure 2:
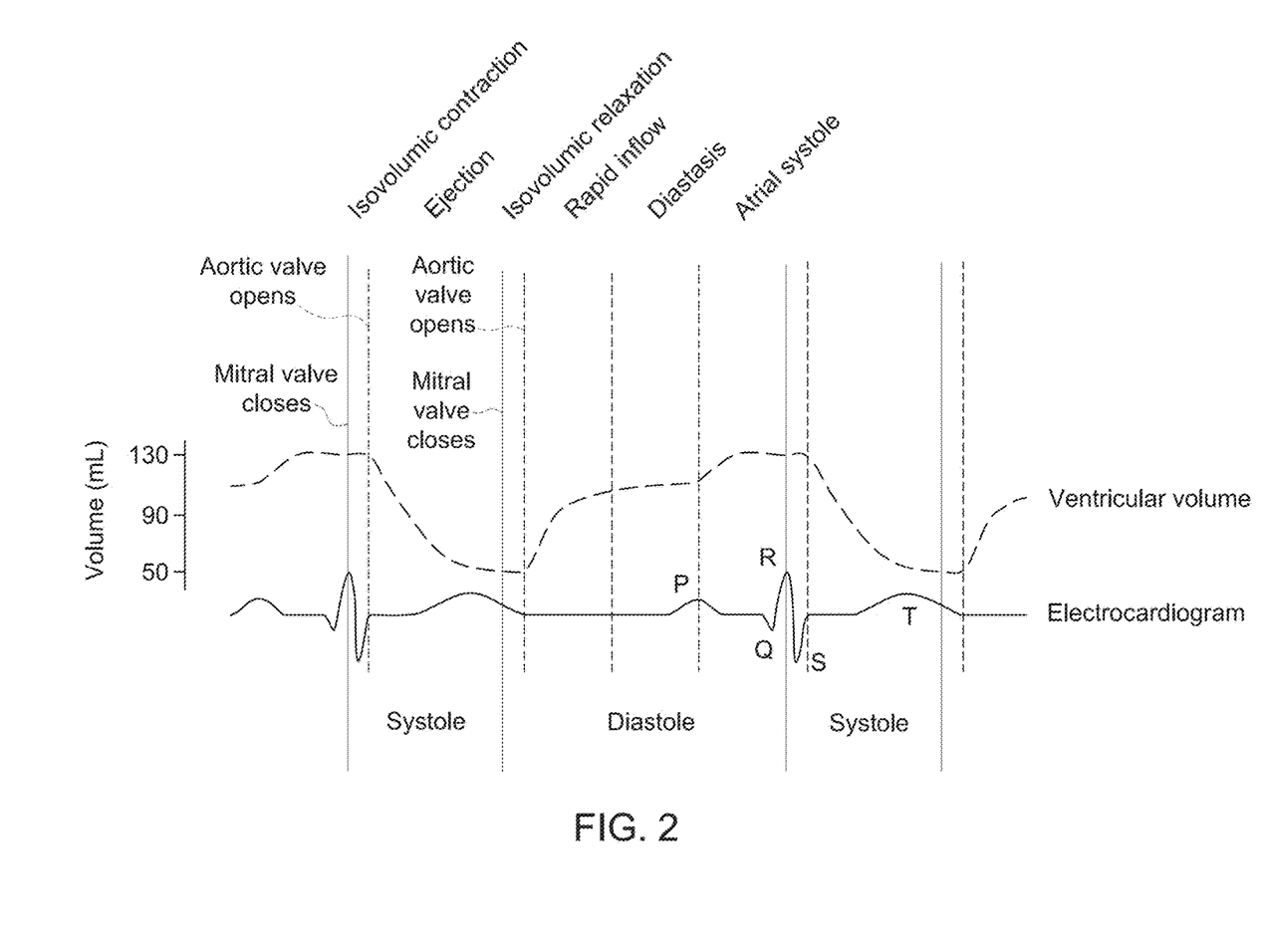
FIG. 2 graphically depicts ventricular volume and an ECG in the context of cardiac phases.

Furthermore, referring to the partial Wiggers diagram shown in FIG. 2, certain heart signals and measurements are shown in line with the main heart phases (systole's isovolumic contractions and ejection, as well as diastole's isovolumic relaxation, rapid inflow, diastasis and atrial systole). One of the depicted curves is ventricular volume, which decreases during systole and increases during diastole.

It may be observed that the shape of the ventricular volume curve compared to the cardiac-cycle signal 118 examples shown in FIG. 4, exhibit a high similarity. In particular, both ventricular volume and the present cardiac-cycle signal 118 start decreasing at the end of the ECG's S wave, increase after the ECG's T wave, and show an inflection around the ECG's P wave. This similarity is not accidental. As mentioned herein, the cardiac-cycle signal 118 is the weighted average of time signals, each related to a low-resolution pixel corresponding to a rectangular region on the original high-resolution ultrasound sequence. During systole, the average brightness in rectangles at the region of the ventricles increases, as they show less blood and more tissue (blood is dark, whereas tissue is bright on echocardiograms). In the present approach, the weights, given by the motion frame, for the ventricular regions are negative. As a result, the cardiac-cycle signal 118 decreases during systole. The opposite happens during diastole. The speed of the ventricular contraction or relaxation is captured in the cardiac-cycle signal 118, which correspondingly features regions such as the diastasis or the inflection point caused by the start of atrial systole, which enables one to visually identify those points in time.

It should be noted, however, that the cardiac-cycle signal 118 does not actually measure volumes (or even areas). The cardiac-cycle signal 118 instead measures brightness variations. These are indeed correlated with volume changes, as explained above, but are not explicitly equivalent. Thus, the cardiac-cycle signal 118 does not provide absolute volume readings, but rather relative readings, which mainly facilitates the identification of points in time, more specifically times related to the heart cycle phases where such brightness changes (and volume changes) occur. Another difference is that, while the ventricular volume does not change during isovolumic phases (thus their name), the cardiac cycle signal 118 does tend to change during these phases, mainly during the isovolumic relaxation, because the heart does move during these phases (though without corresponding changes in volume), and thus these movements are captured by the cardiac cycle signal 118.

Figure 6:
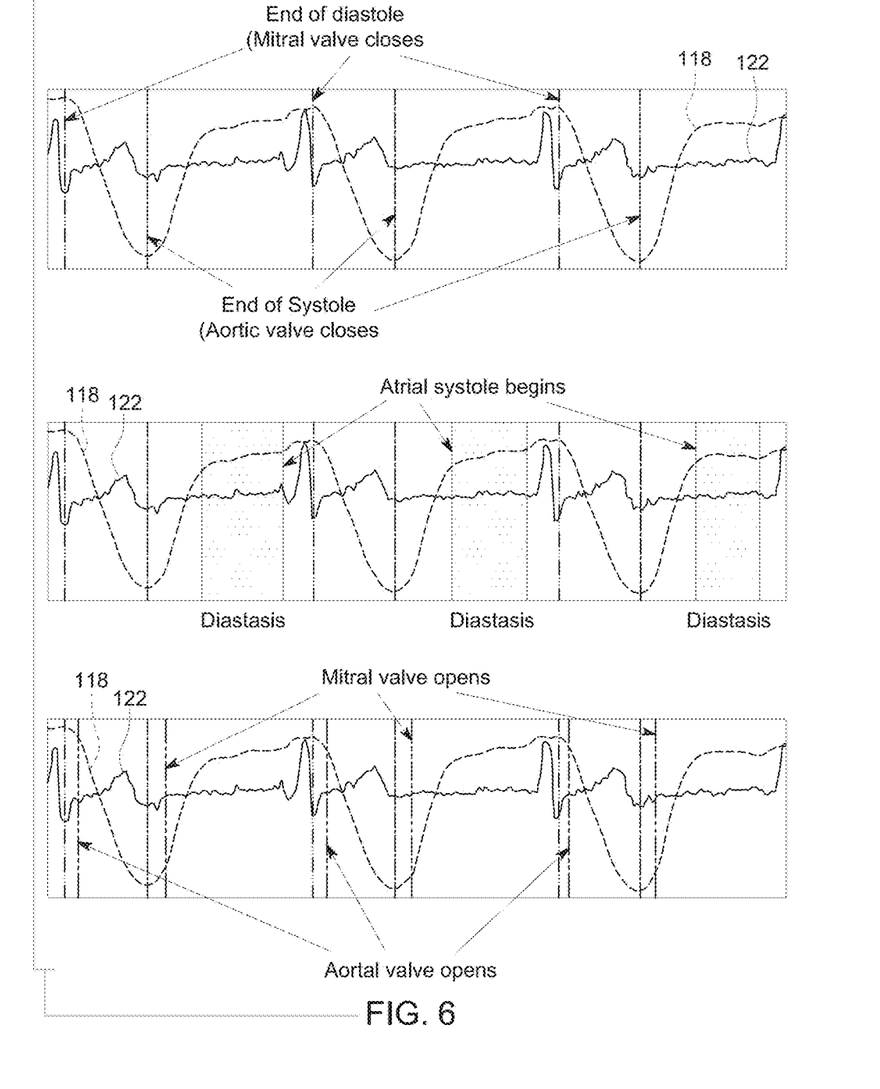
FIG. 6 depicts cardiac phase identifications based on a cardiac-cycle signal, in accordance with aspects of the present disclosure.

Turning to FIG. 6, this figure depicts how to identify the different heart cycle phases on the cardiac-cycle signal 118. It is relatively easy to identify the end of diastole (when the mitral valve closes), the end of systole (when the aortic valve closes) (both shown in the uppermost illustration), the rapid inflow, the diastasis, and the atrial systole, (shown in the middle illustration) as they are usually prominent on the cardiac-cycle signal 118. In some instances, one can also identify the moments when the mitral valve opens or the aortic valve opens (end of the isovolumic contraction and isovolumic relaxation, respectively), as slight inflections on the cardiac-cycle signal 118 (shown in the bottom illustration). However, these inflections are not prominent, and are not always sufficiently discernible.

Another property of the cardiac-cycle signal 118 computation is its robustness. Typically, changes in the algorithm parameters and input scope do not significantly impact the aspects of the resulting curve corresponding to temporal events. Indeed, despite such changes, the obtained cardiac-cycle signals 118 are consistent in their temporal features. The cardiac-cycle signal 118 is also robust to spatial cropping, ignores overlay features (such as labels, logos and ECG plots), and is not sensitive to the fact that the relevant sequence information may be contained only inside the conic portion of the displayed frames. In addition, the algorithm is able to extract the above discussed cardiac-cycle signal 118 for most levels of image quality, and for most views of the heart.

It may also be noted that the cardiac-cycle signal 118 significantly resembles strain-rate curves, which are also highly correlated with ventricular volume in typical cases. Strain-rate curves characterize myocardial function, measuring the amount of tissue strain and relaxation during systole and diastole, respectively. The advantage of the cardiac-cycle signal 118 over strain-rate curves is that of computational simplicity, which directly influences computation speed and real-time implementation. As discussed in the introduction, strain rate curves typically require high-resolution images, with good-to-high quality, and complex image processing. In contrast, as discussed herein, the cardiac-cycle signal 118 computation is fast and straightforward, and does not require good image quality, as it does not look for any spatial features on the echocardiogram. Thus, the cardiac-cycle signal 118 achieves high degree of robustness in real-time.

Online Computation—With respect to online implementation of the present approach it may be appreciated that equation (2) enables such an online implementation. In particular, in this example, the basic algorithm set forth in FIG. 3 may be run on a relatively small number (e.g., ten) of frames (i.e., images 42) to obtain the motion frame 120. From this point on, the cardiac-cycle signal 118 can be computed sample-by-sample by projecting each new echocardiogram frame x(t) into the un-normalized motion frame $v_2/\sigma_2$, via $u_2(t)=x(t) \cdot v_2/\sigma_2$, where the dot refers to the dot product. As the projection is significantly faster than the SVD computation, one can perform it at frame rate. From time to time, the motion frame 120 should be re-calculated to avoid drifting errors. Care should be taken to avoid computing the motion frame 120 during diastasis, as there is no significant motion during that phase, thus an erroneous motion frame 120 could be computed.

Motion Frame Approximation—Other techniques are also contemplated to speed up the algorithm. For example, in instances where one is interested in relatively large values of N and/or M (the low-resolution frame dimensions), such as N=M=128, the speed of the overall algorithm may be increased by using an algorithm for eigenvector approximation, rather than actually computing the SVD.

One popular algorithm for eigenvector approximation is the Power Iteration algorithm, through which one starts from an approximate $X^tX$ eigenvector $b_0$, and recursively computes:

$$b_{i+1} = \frac{b_i \cdot X^t X}{\|b_i \cdot X^t X\|} \qquad (6)$$

until convergence.

As one possible initial approximation $b_0$, one can compute:

$$\tilde{b}=\text{diag}(XX^T) \cdot X \qquad (7)$$

and set $b_0$ to the normalized version of $\tilde{b}$, i.e., $b_0=\tilde{b}/\|\tilde{b}\|$.

Likewise, one can approximate the cardic-cycle signal 118 using the Power Iteration algorithm. To this end, one starts from an approximate $XX^t$ eigenvector $c_0$, and recursively computes:

$$c_{i+1} = \frac{XX^t \cdot c_i}{\|XX^t \cdot c_i\|} \qquad (6)$$

until convergence.

As one possible initial approximation $c_0$, one can compute:

$$\tilde{c}=X \cdot \text{diag}(X^TX)^T \qquad (7)$$

and set $b_0$ to the normalized version of $\tilde{c}$, i.e., $c_0=\tilde{c}/\|\tilde{c}\|$.

Using this initialization, a very-close approximation to the cardiac-cycle signal 118 is usually obtained within 3 iterations.

Data Filtering—Further enhancements of the cardiac-cycle signal algorithm may include data filtering. For example, in order to reduce (but not necessarily eliminate) the impact of alien movements and brightness changes on the cardiac-cycle signal computation, one can add signal filtering to the basic algorithm. This may be desirable to reduce or otherwise minimize instances where the cardiac-cycle signal fails to appropriately capture the cardiac cycle due to the superposition of movements other than those related to the cardiac cycle (which may be due to probe movement during acquisition) or due brightness changes on the echocardiogram (which may be due to a user changing the machine's image brightness during acquisition).

In one example of data filtering, in one study a high-pass filter was implemented by subtracting the original signal from a convolved version of itself, where the convolution kernel is of size forty (or other suitable window size) samples. In this example, to address issues related to applying such an approach at the extremities of the cardiac-cycle signal 118 (when the kernel partially exits the cardiac-cycle signal 118 signal during convolution), one approach is to extrapolate the signal at both ends by fitting a straight line on the first forty samples and another at the last forty samples, and using the fitted-line coefficients for the extrapolation.

Cardiac Cycle Signal Simulator—To perform certain additional studies a simulator was implemented to simulate cardiac-cycle signals as discussed herein. In particular, because of the high correlation between the cardiac-cycle signal 118 and the ventricular volume (VV), described above, a MCG/VV generator was implemented that generates signals that follow the ventricular volume characteristics and is normalized between 0 and 1. This generator is useful for developing algorithms for cardiac-cycle signal 118 analysis, and was used in the experiments described below.

In one implementation, the generator receives three sets of parameters: global, local, and noise. The global parameters are used to draw heart cycle parameters for the whole signal, such as the heart rate (HR), number of cycles in the clip, and average relative length of each of six cycle phases (isovolumic contraction, ejection, isovolumic relaxation, rapid inflow, diastasis, and atrial contraction). The given parameters are mean and standard deviations of distributions for each of the above cycle parameters. The local parameters are used to draw deviations of the global cycle parameters for each individual cycle. Thus, the HR does not remain fixed along the signal, but slightly varies from cycle to cycle. The same happens for all the other cycle parameters. The noise parameters are used to add Gaussian noise, as well as a random slight slope for the whole signal. The reason for randomly drawing all these parameters is to allow machine learning (e.g., training of an artificial neural network) to ignore all these variations when learning how to extract the signal HR or cycle phases.

Applications—Various applications of the cardiac-cycle signal are envisioned and are described below. Certain of these applications relate to providing information typically given by ECG signals, such as in situations where ECG acquisition is not possible, desirable or appropriate (such as in many emergency situations). In some applications (as basal plane position estimation), the cardiac-cycle signal 118 provides information not available on the ECG. The cardiac-cycle signal 118 may also be able to enhance ECG for better diagnosis.

Examples of possible applications of the present cardiac cycle signal include, but are not limited to: heart rate determination, determination of heart cycle phases from the signal, echocardiogram sequence editing and navigation (e.g., to allow navigation to key frames or seamless looping of an echocardiogram), arrhythmia detection, basal plane position estimation, and respiratory rate estimation.

Technical effects of the invention include extracting a heart cycle signal from ultrasound sequences (e.g., echocardiograms) without complex spatial image processing and without finding or assuming the knowledge of the position of heart reference points, such as left ventricle center or walls, basal plane, mitral annulus, etc. The algorithm for its computation is fast, straightforward, and robust, and does not rely on complex image processing. It is computed by capturing the temporal changes in low-resolution versions of the echocardiographic frames, such as temporal information of the heartbeat.

Note that applications in other computer vision areas could also benefit from the proposed approach, such as estimating respiratory rate from a video camera or from inferior vena cava (IVC) ultrasound sequences.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for generating a cardiac-cycle signal, comprising:
   accessing or acquiring an echocardiogram comprising a first sequence of image frames;
   resizing each image frame of the first sequence to generate a second sequence of resized image frames;
   generating a first matrix in which one of its dimensions corresponds to a sequence of flattened versions of the resized image frames;
   deriving from the first matrix at least a second matrix, wherein the second matrix is a unitary matrix whose columns or rows are equal to or approximations of singular vectors of the first matrix;
   generating the cardiac-cycle signal using one singular vector of the second matrix; and
   displaying the cardiac-cycle signal on a monitor.

2. The method of claim 1, wherein resizing each image frame of the first sequence comprises spatially downscaling each image frame of the first sequence to a lower resolution.

3. The method of claim 1, wherein deriving from the first matrix to generate the second matrix comprises performing a singular value decomposition.

4. The method of claim 1, wherein generating the cardiac-cycle signal uses the column or row of the second matrix that corresponds to the second largest singular value of the first matrix.

5. The method of claim 4, wherein the column or row of the second matrix that corresponds to the second largest singular value consists of a time signal in the form of a vector corresponding to the heart dynamics present in the echocardiogram.

6. The method of claim 1, further comprising:
   prior to deriving the second matrix from the first matrix, computing an average frame of the sequence of resized image frames and subtracting a flattened version of the average frame from each flattened frame in the first matrix; and
   wherein generating the cardiac-cycle signal uses the column or row of the second matrix that corresponds to the highest singular value of the first matrix.

7. The method of claim 1, wherein the columns or rows of the second matrix are equal to or approximations of left-singular values, wherein a third matrix is additionally derived from the first matrix, wherein the third matrix is an additional unitary matrix whose columns or rows are equal to or approximations of right-singular vectors of the first matrix.

8. The method of claim 7, further comprising:
   generating a motion frame using the column or row of the third matrix that corresponds to the second highest singular value of the first matrix; and
   displaying the motion frame on the monitor.

9. The method of claim 7, further comprising:
   prior to deriving the third matrix from the first matrix, computing an average frame of the sequence of resized image frames and subtracting a flattened version of the average frame from each flattened frame in the first matrix;

generating a motion frame using the column or row of the third matrix that corresponds to the highest singular value of the first matrix; and displaying the motion frame on the monitor.

10. The method of claim 1, further comprising:

inspecting a motion frame to determine if an upper portion of the motion frame is predominantly darker than a lower portion;

if the upper portion of the motion frame is not predominantly darker than the lower portion, the cardiac cycle signal and the motion frame are inverted.

11. The method of claim 1, wherein the cardiac-cycle signal has a period corresponding to an ECG signal acquired concurrently.

12. The method of claim 1, wherein the cardiac-cycle signal is visually similar to a ventricular volume.

13. The method of claim 1, further comprising determining from cardiac-cycle signal one or more of a heart rate, a heart cycle phase, an echocardiogram loop interval, an echocardiogram key frame for navigation, an arrhythmia, a basal plane position estimation, or a respiratory rate estimate.

14. An ultrasound imaging system, comprising:

processing circuitry configured to:

acquire an echocardiogram comprising a first sequence of image frames;

resize each image frame of the first sequence to generate a second sequence of resized image frames;

generate a first matrix in which one of its dimensions corresponds to a sequence of flattened versions of the resized image frames;

derive from the first matrix at least a second matrix, wherein the second matrix is a unitary matrix whose columns or rows are equal to or approximations of singular vectors of the first matrix;

generate the cardiac-cycle signal using one singular vector of the second matrix; and display the cardiac-cycle signal on a monitor.

15. The ultrasound imaging system of claim 14, wherein the first matrix is derived from the second matrix using a singular value decomposition.

16. The ultrasound imaging system of claim 14, wherein the cardiac-cycle signal is generated using the column or row of the second matrix that corresponds to the second largest singular value of the first matrix.

17. The ultrasound imaging system of claim 14, wherein the processing circuitry is further configured to:

prior to deriving the second matrix from the first matrix, compute an average frame of the sequence of resized image frames and subtract a flattened version of the average frame from each flattened frame in the first matrix;

wherein generating the cardiac-cycle signal uses the column or row of the second matrix that corresponds to the highest singular value of the first matrix.

18. The ultrasound imaging system of claim 14, wherein decomposing the first matrix additionally generates a third matrix, wherein the third matrix is an additional unitary matrix whose columns or rows are equal to or approximations of right-singular vectors of the first matrix.

19. The ultrasound imaging system of claim 18, wherein the processing circuitry is further configured to:

generate a motion frame using the column or row of the third matrix that corresponds to the second highest singular value of the first matrix; and display the motion frame on the monitor.

20. The ultrasound imaging system of claim 18, wherein the processing circuitry is further configured to:

prior to deriving the third matrix from the first matrix, compute an average frame of the sequence of resized image frames and subtracting a flattened version of the average frame from each flattened frame in the first matrix;

generate a motion frame using the column or row of the third matrix that corresponds to the highest singular value of the first matrix; and display the motion frame on the monitor.

* * * * *